United States Patent [19]

Hatch

[11] Patent Number: 5,723,619

[45] Date of Patent: Mar. 3, 1998

[54] METHOD FOR THE SYNTHESIS OF DEOXYPYRIDINOLINE

[75] Inventor: Robert P. Hatch, Elkhart, Ind.

[73] Assignee: Bayer Corporation, Elkhart, Ind.

[21] Appl. No.: 782,214

[22] Filed: Jan. 13, 1997

[51] Int. Cl.$^6$ .................. C07D 213/127; C07D 213/16; C07D 213/20

[52] U.S. Cl. .............................. 546/250; 546/300

[58] Field of Search ...................... 546/250, 300

[56] References Cited

U.S. PATENT DOCUMENTS

| | | | |
|---|---|---|---|
| 5,350,855 | 9/1994 | Daniloff et al. | 546/291 |
| 5,502,197 | 3/1996 | Daniloff et al. | 546/278.7 |
| 5,527,715 | 6/1996 | Kung et al. | 436/547 |

OTHER PUBLICATIONS

Auge et al, Tetrahedron Letters, vol. 37, No. 43, pp. 7715–7716 (1996), Lithium Trifluoromethanesulfonate-–catalyzed . . .

Chini et al, Tetrahedron Letters, vol. 31, No. 32, pp. 4661–4664, (1990), Metal Salts as New Catalysts for Mild and Efficient . . .

*Primary Examiner*—Alan L. Rotman
*Attorney, Agent, or Firm*—Jerome L. Jeffers

[57] ABSTRACT

Disclosed is a method for the chemical synthesis of deoxypyridinoline (DPD). The synthesis involves the preparation of a protected 3-hydroxypyridinium starting with a Nα-protected lysine and a 5,6-epoxy-2-N-protected-O-protected-(2S)-2-aminohexanoate with subsequent deprotection to provide the desired DPD.

10 Claims, 1 Drawing Sheet

METHOD FOR THE SYNTHESIS OF DEOXYPYRIDINOLINE

BACKGROUND OF THE INVENTION

Collagen is present in various forms in all tissue. It is now well accepted that collagen has the form of amino acid chains cross-linked by pyridinium cross-links. The pyridinium crosslinks are formed from three hydroxylysine residues, two of which are from the terminal (non-helical) peptides of the collagen molecule that are enzymatically converted to aldehydes before reaction and a third hydroxylysine situated in the helical portion of a neighboring collagen molecule. Two pyridinium crosslinks, pyridinoline (PYD) and deoxypyridinoline (DPD), have been identified. There have been described in the literature techniques for the measurement of pyridinoline in urine by use of enzyme labeled anti-PYD to form a pyridinoline-enzyme labeled complex which can be detected by an enzyme-linked immunosorbant assay. While the analysis for PYD is useful as a means of screening for osteoporosis and rheumatoid arthritis, its presence in connective tissue, as well as in bone, can cause skewed results for the diagnosis of osteoporosis or bone degradation. Accordingly, immunoassays for deoxypyridinoline (DPD), which is only found in bone, have become preferred over those for PYD for the early detection of bone degradation.

BRIEF DESCRIPTION OF DRAWING

Testing for DPD can be carried out by contacting a fluid test sample, e.g. urine, with a labeled antibody specific for DPD. A particularly convenient method for DPD analysis involves the use of a test strip of the type depicted in FIG. 1.

Figure 1:
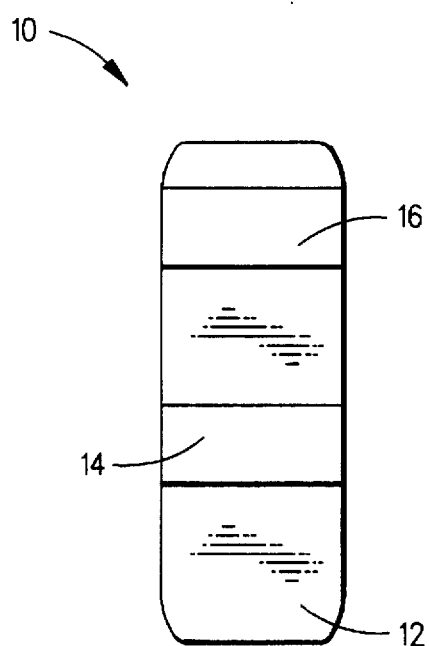
Referring to FIG. 1, strip 10 having a labeled anti-DPD antibody complex (typically with gold sol as the labeling material to provide a gold sol-DPD antibody complex) binds with DPD in the fluid test sample applied to the application zone 12 of the strip 10 and migrates through the first capture zone 14 and second capture zone 16. In the first capture zone 14 there is immobilized DPD which captures unbound, labeled anti-DPD. The labeled antibody, which was not captured in the first capture zone because it combined with DPD in the fluid test sample, is captured in the second capture zone 16 by anti-DPD antibodies which are immobilized in this zone. The DPD concentration in the test sample can be determined by spectrophotometrically measuring the amount of labeled DPD captured in the first capture zone 14, or more accurately by use of an algorithmic treatment of reflectance measurements from both zones 14 and 16.

The first capture zone 12 requires immobilized DPD with which the labeled anti-DPD, which hasn't reacted with DPD in the fluid sample, can combine to become immobilized in this capture zone. This sort of disposable test system requires the use of considerable amounts of DPD which, when obtained from animal bone, is quite expensive. The expense involved with the procurement of natural DPD has led to attempts to synthesize this material and thereby reduce the cost of diagnostic test strips which employ DPD in DPD detection systems.

One method for the synthesis of DPD as well as PYD and derivatives thereof is disclosed in published European Patent Application 0 556 152 $A_1$. In this procedure a compound of the formula:

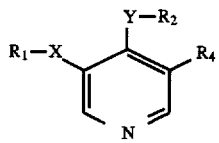

is reacted with an R group which is defined as $X_5$—$CH_2$—$CHX_1$—$Z$—$R_3$ wherein the R, X, Y and Z groups are selected to provide DPD, PYD or various derivatives thereof. In each case, the pyridine ring is formed before the addition of the side chain to the nitrogen atom. In the process for the preparation of DPD of the present invention fewer steps are involved because it is not necessary to separately prepare $X_5$—$CH_2$—$CHX_1$—$Z$—$R_3$ thereby providing a less labor intensive method.

DESCRIPTION OF THE INVENTION

The synthesis of DPD contemplated by the present invention involves the steps of:

a) reacting a Nα-protected-O-protected lysine (compound 1, Scheme 1) with at least two equivalents of 5,6-epoxy-2-N-protected-O-protected(2S)-2-aminohexanoate (compound 5, scheme 1) in an appropriate solvent to produce the corresponding aminodiol (compound 6, scheme 1). Suitable solvents include acetonitrile, methanol and water/alcohol. In Scheme 1, there is depicted lithium perchlorate as an additive which is provided for the purpose of catalyzing the reaction. Two equivalents of the epoxide per equivalent of the aminohexanoate are required because dialkylation is the required process.

b) The aminodiol 6 is then oxidized with a suitable oxidizing agent, such as oxalyl chloride-DMSO in a suitable solvent such as methylene chloride to provide the corresponding aminodiketone (compound 7, scheme 1). Suitable oxidizing agents other than oxalyl chloride-DMSO include thionyl chloride-DMSO, trifluoroacetic anhydride-DMSO and acetic anhydride-DMSO. Suitable solvents, other than methylene chloride include diethyl ether, tetrahydrofuran and chloroform.

c) The aminodiketone of step (b) is further reacted with a base such as sodium hydroxide in alcohol or a tertiary amine, e.g. triethylamine to produce the 3-hydroxydihydropyridine which is combined with an oxidizing agent such as the base (DBN) in the presence of $O_2$ in a suitable solvent such as methylene chloride to form the 3-hydroxypyridine ring to provide pyridinium product 8 in scheme 1. Other suitable oxidizing agents include dicyanodichloroquinone (DDQ), bromine or $MnO2$ whereas the reaction can be carried out in other solvents, such as methylene chloride, acetic acid or methanol. Product 8 is deprotected to provide deoxypyridinoline.

Scheme 1
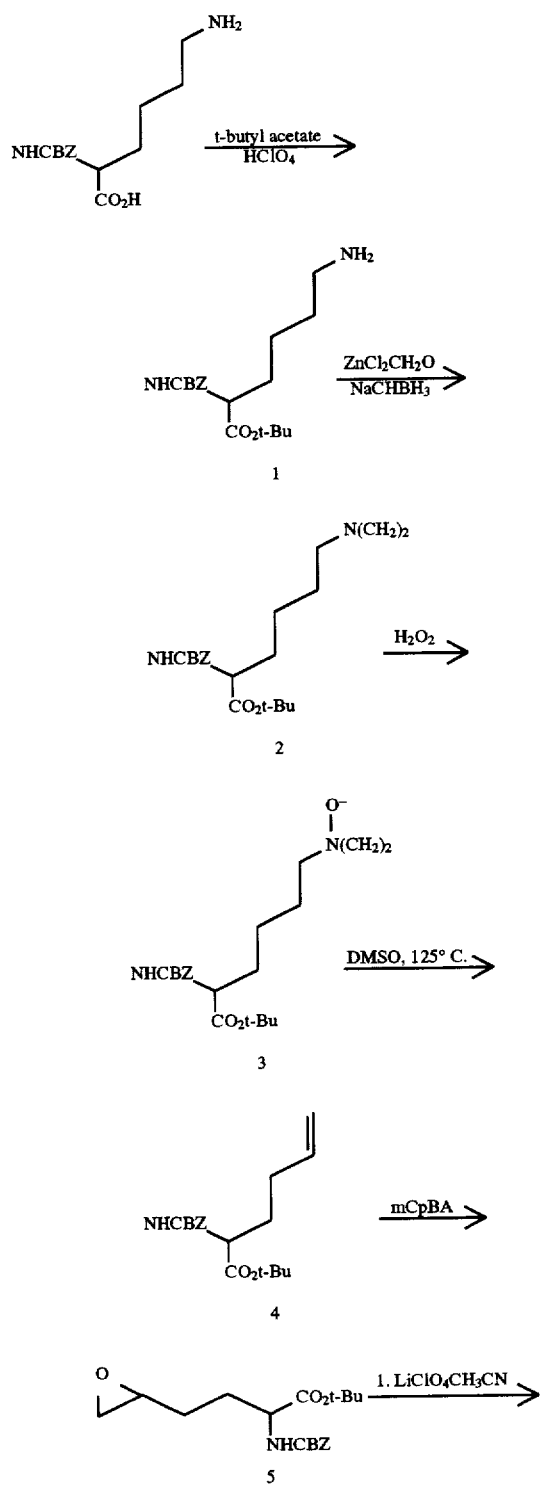
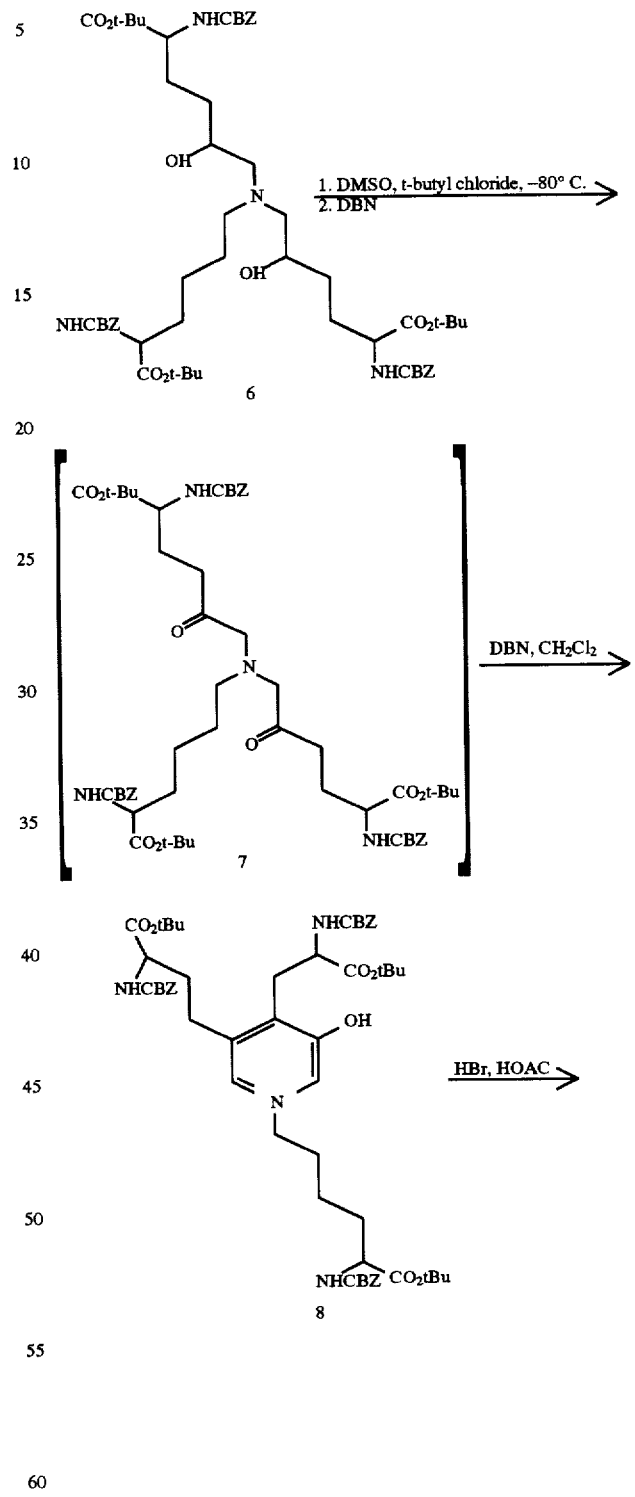

-continued
Scheme 1

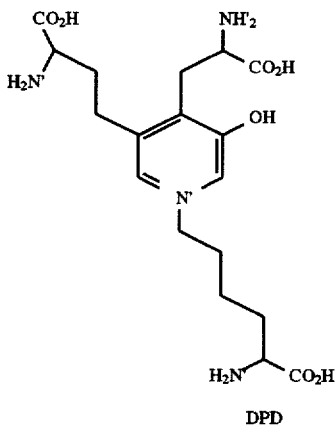

DPD

The present invention is further illustrated by the following example.

EXAMPLE

A. Preparation of Nα-CBZ-O-t-butyl L-lysine (1)

A mixture of 25 g of Nα-CBZ-L-lysine from Sigma, where CBZ is benzyloxycarbonyl, 250 mL of t-butyl acetate and 14 mL of 70% perchloric acid was vigorously mixed until all solids were dissolved. After stirring overnight, 375 mL of ethyl acetate was added followed by 250 mL of water. The pH of the aqueous layer was raised to 5.5 with 20% NaOH whereupon the organic phase was separated. The aqueous phase was extracted with the ethyl acetate solution and the pH again raised to 10.5 whereupon it was again extracted with 200 mL of fresh ethyl acetate. The organic extracts were combined, washed with saturated brine, dried over $Na_2SO_4$ and concentrated. The residue was dried overnight under high vacuum to yield 23.2 g of a colorless, viscous material.

$^1$HNMR (60 Mhz, $CDCl_3$)δ: 7.35 (s,5H), 5.1 (s,2H), 4.2 (m, 1H), 3.1 (m,2H) 1.4 (s,9H), 2.1–1.4 (m,4H).

B. Nε-dimethylamino-Nα-CBZ-O-t-butyl L-lysine (2)

A mixture consisting of 3.7 (27.2 mmol) of $ZnCl_2$, 3.2 g (53 mmol) of $NaCNBH_3$ and 60 mL of methanol was prepared to which was added a solution of 18 g (51.7 mmol) of the amine 1 in 180 mL of methanol. After cooling to 10°–15° C. 12.4 mL of 37% formaldehyde (165 mmol) was added dropwise over a 2–3 minute period. The reaction was stirred for 1 hour and monitored by silica gel TLC with elution using a 60:10:1(v/v/v/) mixture of chloroform/methanol/concentrated ammonia (solvent A). One hundred milliliters of water was added and the mixture concentrated to a volume of 200 ml. Ethyl acetate (200 mL) was added and the pH raised to 10.5 with 10% NaOH. The ethyl acetate was separated and the pH of the aqueous phase readjusted to 10.5 and extracted with 200 mL of fresh ethyl acetate. The ethyl acetate extracts were combined, washed with NaCl, dried over $Na_2SO_4$, filtered and concentrated to yield, after drying overnight under high vacuum, 14.86 g of viscous oil.

$^1$HNMR (300 Mhz, $d_6$DMSO) δ: 7.56(d,1H), 7.35(s,5H), 5.05(s,2H), 3.85(m,1H), 2.15(t,2H), 2.08(s,6H) 1.60(d of t,2H), 1.40(s,9H), 1.35 (m,4H).

C. Nε-dimethylamino-Nα-CBZ-O-t-butyl L-lysine N-oxide (3)

A solution of 25.3 g of dimethylamine 2, 7.9 mL of 30% hydrogen peroxide and 150 mL of methanol was stirred for 5 h after which an additional 7.9 g of 30% hydrogen peroxide was added. The reaction was allowed to stir for 48 h and monitored by silica gel TLC, eluting with solvent A. A 1 mL aqueous slurry of approximately 5 mg of platinum black was added whereupon the reaction was stirred for 7 h and another slurry of 5–10 mg platinum black added. The mixture was stirred overnight and monitored for peroxides using peroxide test paper with warming to 60° C. to remove peroxides when necessary. Once the reaction tested negative for peroxides, the mixture was filtered and concentrated. The residue was dissolved into 300 mL of EtOAc, dried over $Na_2SO_4$, filtered, concentrated and chromatographed on 400 g of silica gel, eluting with Solvent A to produce 13 g of product as a colorless oil.

$^1$HNMR (300 Mhz, $d_6$DMSO)δ: 7.78(d,1H), 7.37(s,5H), 5.05(dd,2H), 2.88(m, 1H) 3.05(t,2H,) 2.95(s,6H) 1.70(m, 4H), 1.40(s,9H) 1.32(m,2H).

The synthesis of this Nα-protected-O-protected lysine is known in the literature (Scott et al. Commun., 1981, 11(4) 303–314.

D. N-CBZ-2-amino-5-hexenoate-5-t-butyl ester (4)

A solution of 14.8 g of N-oxide 3 in 250 mL of DMSO was warmed to 125° C. for 2 h while sparging with argon. The DMSO was distilled at 70° C. under high vacuum. Chromatography of the residue on 450 mL of silica gel, eluting with 20:80 (v/v) of EtOAc/hexane, produced the product in fractions 70–120 (18 mL fractions). These were combined and concentrated to yield 3.15 g of the product as a colorless oil.

$^1$HNMR ($d_6$DMSO) δ: 7.62(d,1H) 7.35(s,5H) 5.78(m, 1H), 5.08(dd,2H), 4.98(m,2H) 3.86(m, 1H) 2.08(dt,2H) 1.68 (m,2H), 1.38(s,9H) 1.35(m,2H).

E. N-CBZ-2-amino-5,6-epoxy-hexanoate-5-t-butylester (5) cf. Cpd. 4 (Step D)

The 85% m-chloroperbenzoic acid (mCpBA) from Aldrich Chemical Co. was purified by dissolving in methylene chloride and washing with pH 7.5 buffer. The organic layer was separated, dried over $Na_2SO_4$, filtered and concentrated. The solid was dried overnight under high vacuum and stored at 3° C.

A mixture of 3.15 g of the hexanoate 4 (9.75 mmol) and 1.76 g of mCpBA, (10.2 mmol) in 25 mL of methylene chloride was stirred for 48 h at room temperature. The reaction was diluted with 125 mL of EtOAc and washed twice with 5% NaOH and then brine. After drying over $Na_2SO_4$, the reaction was filtered and concentrated to produce 2.9 g of the product as a colorless oil.

$^1$HNMR ($d_6$DMSO) δ: 7.35(s,5H) 5.05(s,2H) 3.90(m, 1H), 2.65(m,1H) 2.50(m,1H) 2.42(m,1H) 1.8–1.5(m,2H) 1.40(s,9H) 1.35(m,2H).

MS(FAB): 358 ($M^+ + Na^+$)

F. 2,12-Benzyloxycarbonylamino-7-(5-benzyloxycarbonyl-amino-5-t-butoxycarbonyl-pentyl)aza-1,13-di-t-butyl-5,9-dihydroxy-tridecanodiate (6)

Epoxide 5 (1.68 g, 5.01 mmol) was dissolved in 1.5 mL of dry acetonitrile after which 0.53 g (5.01 mmol) of anhydrous $LiClO_4$ was added. When the solid dissolved 0.8 g (23 mmol) of amine 1 in 1.5 mL of acetonitrile was added. The mixture was stirred at 50° C. overnight and then concentrated under reduced pressure. The residue was chromatographed on 150 g of silica gel, eluting with 7:1 (v/v)

chloroform/solvent A to produce 1 g of aminodiol 6 and 0.5 g of recovered epoxide. The diol was dissolved in a known amount of methylene chloride and stored over 3 Å molecular sieves for later use.

MS(FAB): 1007(M⁺)

G. 3-Hydroxy-1-(5-benzyloxycarbonylamino-5-t-butoxycarbonyl-pentyl)-4-(2-benzyloxycarbonylamino-2-t-butoxycarbonyl-ethyl)-5-(3-benzyloxycarbonylamino-3-t-butoxycarbonyl-propyl) pyridinium salt (8)

To 1 mL of methylene chloride was added 0.6 mL of 2M (1.2 mmol) oxalyl chloride in methylene chloride and the mixture cooled to −55° C. Dimethylsulfoxide (DMSO) (78 µL, 1.1 mmol) in 0.25 mL of methylene chloride was then added dropwise. After 15 minutes, 400 mg of the diol 6 in 1 ml of methylene chloride was added dropwise. The mixture was warmed to −30° C. while stirring for 20 minutes and the reaction was then cooled back to −55° C. whereupon 0.26 g (2.6 mmol) of triethylamine was added. The reaction was allowed to warm to room temperature and was then diluted with 25 mL of EtOAc, washed with 5% NaOH followed by brine and dried over $Na_2SO_4$. After filtering, the solution was concentrated to yield 0.39 g of 2,12-benzyloxycarbonylamino-7-(5-benzyloxycarbonylamino-5-t-butoxycarbonyl-pentyl)aza-1,13-di-t-butyl-5,9-dioxo-tri-decanodiate 7 which was not characterized due to its instability. The residue was dissolved in 4 mL of methylene chloride and 0.25 g of diazabicyclo[4.3.0]non-5-ene (DBN) added. The mixture was stirred overnight protected by a drying tube. Acetic acid (100 µL) was added and the solvent evaporated. The residue was chromatographed on 100 g of silica gel eluting with 20:1:0.5 chloroform/methanol/acetic acid. Fractions 11–14 (18 mL fractions) contained 0.26 g of pyridinium product 8.

H. Deoxypyridinoline (DPD)

A mixture of 160 mg of the pyridinium acetate 8 and 1 mL HBr in HOAc was stirred for 30 minutes and then an additional 1 mL of HBr/HOAc was added. After 1 h the solvent was removed and the residue dissolved into 50 mL of a 4:1:1 (v/v/v) mixture of n-butanol/water/HOAc (solvent B) after which 5 g of fibrous cellulose was added. The suspension stood for 30 minutes and was filtered followed by the addition of 3 more grams of cellulose to the filtrate and additional filtering after 2 hours. The two cellulose solids were combined and slurried in 50 mL of water and filtered after 30 minutes. An aliquot was removed whose absorbance in pH 8 buffer at 326 nm using a 5290 molar extinction coefficient and molecular weight of 413 indicated 28 mg of DPD. The solution was lyophilized and the residue dissolved in 10 mmol HCl and 8 g of washed BioRad AG-1X10(Cl⁻ form). After 1 h the resultant was filtered and the filtrate concentrated to dryness on a Savant Speed-Vac® concentrator to yield 56 mg of the very hygroscopic tetra-chloride salt.

¹HNMR (300 Mhz d₆DMSO) δ: 8.65(s,1H), 8.50(s,1H), 4.51(t,2H, J=7.5) 4.28(t,1H,J=7) 4.10(t,1H,J=6) 3.99(t,1H, J=7) 3.4(m,2H) 3.2–2.9 (m,2H) 2.2(m,2H) 2.1(m,2H) 2.0 (m,2H) 1.5–1.3(m,2H)

The O-t-butyl esters and CBZ protective groups may be removed by a variety of treatments familiar to one skilled in this art as described by Greene et al in Protective Groups in Organic Synthesis; John Wiley & Sons: New York, 1991:Pp 246 and 335–7. Thus, the t-butyl ester may be removed using other acids such as formic, hydrochloric, P-toluenesulfonic, trifluoromethanesulfonic, methanesulfonic and trifluoroacetic. The CBZ group may be removed by a variety of methods such as, for example; by hydrogenolysis, with Lewis acids such as aluminum chloride, trimethylsilyl iodide and boron tribromide; photolysis; electrolysis; barium hydroxide or by the use of other acids such as trifluorosulfonic acid and methanesulfonic acid.

I claim:

1. A method for the preparation of deoxypyridinoline which comprises the steps of:

(a) reacting an Nα-protected-O-protected lysine of the formula:

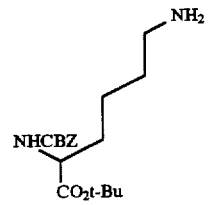

with at least two equivalents of 5,6-epoxy-2-N-protected-O-protected-(2S)-2-aminohexanoate of the formula:

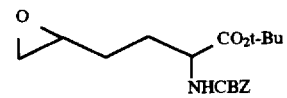

to produce the corresponding aminodiol of the formula:

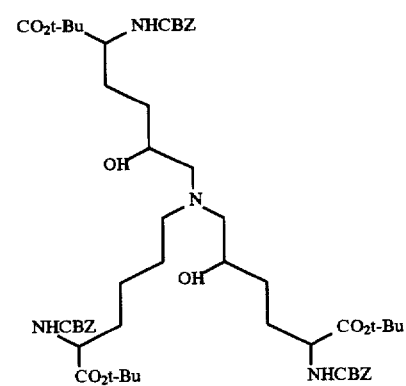

b) reacting the aminodiol with an oxidizing agent to provide the corresponding aminodiketone of the formula:

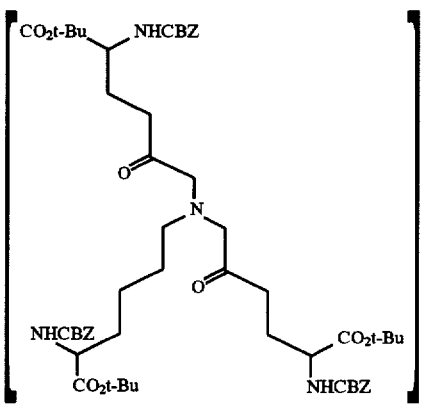

c) reacting the aminodiketone with a base to produce the corresponding 3-hydroxydihydropyridine and then reacting the 3-hydroxydihydropyridine with an oxidizing agent to form the 3-hydroxypyridinium ring thereby providing a compound of the formula:

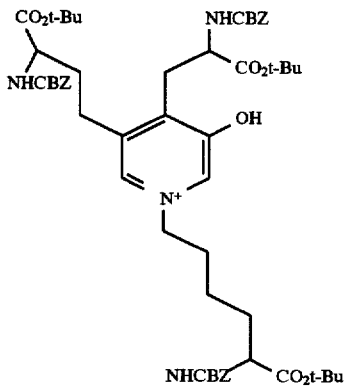

and d) deprotecting the compound of step (d) to provide deoxypyridinium of the formula:

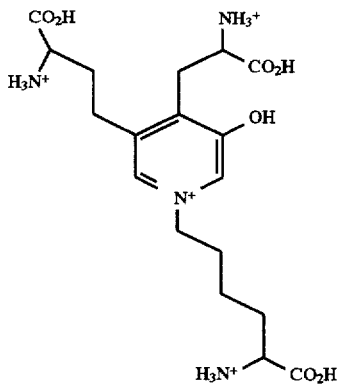

2. The method of claim 1 wherein all of the intermediate products are recovered and purified with the exception of the aminodiketone.

3. A method for the preparation of deoxypyridinoline which comprises the steps of:
   a) Reacting at least two equivalents of N-CBZ-2-amino-5,6-epoxy-hexanoate-5-t-butyl ester in an appropriate solvent with Nα-CBZ-O-t-butyl L-lysine to provide 2,12-benzyloxycarbonylamino-7-(5-benzyloxycarbonylamino-5-t-butoxycarbonylpentyl)aza-1,13-di-t-butyl-5,9-dihydroxy-tridecanoate and recovering this diol;
   b) reacting the diol prepared in step (a) with a suitable oxidizing agent in an appropriate solvent to provide 2,12-benzyloxycarbonylamino-7-(5-benzylcarbonylamino-5-t-butoxycarbonyl-pentyl)aza-1,13-di-t-butyl-5,9-dioxo-tridecanodoate, and
   c) without its isolation, reacting the tridecanoate with a base to provide 3-hydroxy-1-(5-benzoxycarbonylamino-5-t-butoxycarbonyl-pentyl)-4-(2-benzyloxycarbonylamino-2-t-butoxycarbonyl-ethyl)-5-(3-benzyloxycarbonylamino-3-butoxycarbonylpropyl) pyridinium salt; and
   d) reacting the pyridinium salt prepared in step (c) with HBr in an appropriate solvent to provide deoxypyridinoline.

4. The method of claim 3 wherein the reaction of step (a) is carried out in acetonitrile, methanol or a combination of water and alcohol as solvent.

5. The method of claim 3 wherein lithium perchlorate is included in step (a) as a catalyst and acetonitrile as the solvent.

6. The method of claim 3 wherein the oxidizing agent in step (b) is oxalyl chloride-DMSO, thionyl chloride-DMSO, trifluoroacetic anhydride-DMSO or acetic anhydride-DMSO.

7. The method of claim 6 wherein the oxidizing agent is oxalyl chloride-DMSO.

8. The method of claim 3 wherein the solvent in step (b) is methylene chloride, diethyl ether, tetrahydrofuran or chloroform.

9. The method of claim 3 wherein the base in step (c) is triethylamine.

10. A method for the preparation of deoxypyridinoline which involves
   a) reacting an Nα-protected-O-protected lysine with at least two equivalents of 5,6-epoxy-2-N-protected-O-protected (2S)-2-aminohexanoate in an appropriate solvent to produce the corresponding aminodiol;
   b) reacting the amino diol with an oxidizing agent to provide the corresponding aminodiketone;
   c) reacting the aminodiketone with a base to produce the corresponding 3-hydroxydihydropyridinoline compound as an intermediate and then reacting this intermediate with an oxidizing agent to form the corresponding pyridinium compound; and
   d) deprotecting the pyridinium compound to provide deoxypyridinoline.

* * * * *